United States Patent

Pfiffner et al.

Patent Number: 5,710,314
Date of Patent: Jan. 20, 1998

[54] MICROBICIDES

[75] Inventors: Albert Pfiffner, Bülach, Switzerland; Stephan Trah, Freiburg, Germany

[73] Assignee: Novartis Corporation, Summit, N.J.

[21] Appl. No.: 460,397

[22] Filed: Jun. 2, 1995

[30] Foreign Application Priority Data

Sep. 30, 1994 [CH] Switzerland ............... 2967/94

[51] Int. Cl.$^6$ ............... C07C 69/76; C07C 233/00; A01N 37/12

[52] U.S. Cl. ............... 560/60; 560/55; 560/35; 564/167; 514/539; 514/532; 514/619; 514/622

[58] Field of Search ............... 560/60, 55, 35; 564/167; 514/532, 539, 619, 622

[56] References Cited

U.S. PATENT DOCUMENTS

| | | | |
|---|---|---|---|
| 5,145,980 | 9/1992 | Wenderoth et al. | 560/35 |
| 5,393,782 | 2/1995 | Wingirt et al. | 514/599 |

FOREIGN PATENT DOCUMENTS

| | | | |
|---|---|---|---|
| A278595 | 8/1988 | European Pat. Off. | |
| 95/173766 | 6/1995 | WIPO | |

Primary Examiner—Paul Killos
Attorney, Agent, or Firm—Hesna J. Pfeiffer; Edward McC. Roberts

[57] ABSTRACT

Compounds of formula I

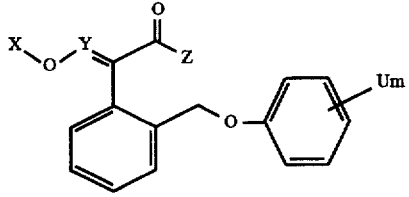

and possible isomers and isomeric mixtures thereof, wherein
a)
  X is $CH_2F$ or $CHF_2$;
  Y is CH and
  Z is OMe, or
b)
  X is $CH_2F$ or $CHF_2$;
  Y is a nitrogen atom and
  Z is OMe or $NHCH_3$,
and wherein also
m is 0, 1, 2, 3, 4 or 5 and
U represents identical or different substituents selected from halogen, cyano, nitro, $C_1$-$C_{12}$alkyl, $C_3$-$C_8$cycloalkyl, $C_3$-$C_6$alkenyl, $C_3$-$C_6$alkenyloxyiminomethyl, $C_1$-$C_4$alkoxy, $C_1$-$C_4$alkoxyiminomethyl, $C_1$-$C_2$haloalkyl, $C_1$-$C_2$haloalkoxy, unsubstituted or substituted phenyl, unsubstituted or substituted phenoxy and unsubstituted or substituted benzyl or represents substituents at two adjacent positions of the phenyl ring of formula I that define a fused hydrocarbon bridge so as to form a larger hydrocarbon ring having up to 14 carbon atoms, are suitable for controlling and preventing microorganisms, insects and Acarina on plants.

They can be used in the form of commercially customary formulated compositions.

10 Claims, No Drawings

MICROBICIDES

The present invention relates to novel phenyl ether derivatives of formula I below. It relates also to the preparation of those compounds and to agrochemical compositions comprising at least one of those compounds as active ingredient. The invention also relates to the preparation of the mentioned compositions and to the use of the active ingredients or of the compositions in the control of plant-destructive microorganisms, especially fungi, noxious insects and Acarina.

The compounds according to the invention correspond to the general formula I

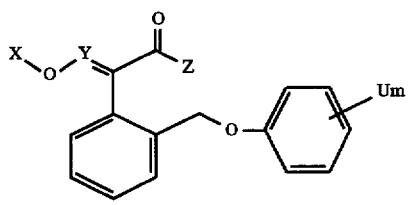

and possible isomers and isomeric mixtures thereof, wherein
a)
X is $CH_2F$ or $CHF_2$;
Y is CH and
Z is OMe, or
b)
X is $CH_2F$ or $CHF_2$;
Y is a nitrogen atom and
Z is OMe or $NHCH_3$,
and wherein also
m is 0, 1, 2, 3, 4 or 5 and
U represents identical or different substituents selected from halogen, cyano, nitro, $C_1$–$C_{12}$alkyl, $C_3$–$C_8$cycloalkyl, $C_3$–$C_6$alkenyl, $C_3$–$C_6$alkenyloxyiminomethyl, $C_1$–$C_4$alkoxy, $C_1$–$C_4$alkoxyiminomethyl, $C_1$–$C_2$haloalkyl, $C_1$–$C_2$haloalkoxy, unsubstituted or substituted phenyl, unsubstituted or substituted phenoxy and unsubstituted or substituted benzyl or represents substituents at two adjacent positions of the phenyl ring of formula I that define a fused hydrocarbon bridge so as to form a larger hydrocarbon ring having up to 14 carbon atoms.

If there are asymmetrical carbon atoms present in the compounds of formula I, the compounds occur in optically active form. Purely on the basis of the presence of double bonds the compounds will in any case occur in the [E]- and/or [Z]-form. Atropisomerism may also occur. Formula I is intended to encompass all those possible isomeric forms and also mixtures thereof, for example racemic mixtures and any [E/Z]-mixtures.

At room temperature the compounds of formula I are stable oils, resins or solids.

The compounds according to the invention exhibit fungicidal, insecticidal and acaricidal properties and are suitable as active ingredients in crop protection. The fungicidal activity is especially pronounced. They can be used in the agricultural sector or related fields preventively or curatively in the control of plant-destructive microorganisms. The compounds of formula I according to the invention are distinguished at low rates of concentration not only by outstanding insecticidal and fungicidal activity but also by being especially well tolerated by plants.

Compounds I having at least one basic centre are capable of forming acid addition salts. Those salts are formed, for example, with strong inorganic acids, such as mineral acids, for example sulfuric acid, a phosphoric acid or a hydrohalic acid, with strong organic carboxylic acids, such as unsubstituted or substituted, for example halo-substituted, $C_1$–$C_4$alkanecarboxylic acids, for example acetic acid, or unsaturated or saturated dicarboxylic acids, for example oxalic, malonic, maleic, fumaric or phthalic acid, or hydroxycarboxylic acids, for example ascorbic, lactic, malic, tartaric or citric acid, or benzoic acid, or with organic sulfonic acids, such as unsubstituted or substituted, for example halo-substituted, $C_1$–$C_4$alkanesulfonic or arylsulfonic acids, for example methanesulfonic or p-toluenesulfonic acid. Owing to the close relationship between the compounds I in free form and in the form of their salts, hereinbefore and hereinafter any reference to the free compounds I or their salts is to be understood as including also the corresponding salts or the free compounds I, respectively, as appropriate and expedient.

Unless defined otherwise, the general terms used hereinbefore and hereinafter have the meanings given hereinbelow.

Alkyl groups on their own or as a structural element of other groups are straight-chained or branched depending on the number of carbon atoms. $C_1$–$C_{12}$alkyl is, for example, methyl, ethyl, propyl, isopropyl, butyl, isobutyl, sec-butyl, tert-butyl, pentyl, hexyl, octyl, decyl, dodecyl or isomers thereof.

Alkenyl as a group is either straight-chained, for example ethenyl, propen-1-yl or but-1-en-1-yl, or branched, for example propen-2-yl or but-1-en-2-yl.

Cycloalkyl is, for example, cyclopropyl, cyclobutyl, cyclopentyl, cyclohexyl or cyclooctyl.

Unsubstituted or substituted phenyl, phenoxy or benzyl are, for example, radicals such as $C_1$–$C_4$alkylphenyl, haloalkylphenyl, halophenyl, $C_1$–$C_4$alkylphenoxy, halophenoxy, $C_1$–$C_4$alkylbenzyl, halobenzyl and so on. Unsubstituted or substituted fused rings are, for example, naphthyl, tetralinyl, decalinyl, fluorenyl, etc.

Halogen is fluorine, chlorine, bromine or iodine. Examples of haloalkyl and haloalkoxy groups are —$CH_2F$, —$CHF_2$, —$CF_3$, —$CH_2Cl$, —$CHCl_2$, —$CCl_3$, —$CCl_2CCl_3$, —$CH_2Br$, —$CH_2CH_2Br$, —$CHBrCl$, —$OCHF_2$, —$OCF_3$, —$OCH_2CF_3$, —$OCF_2CHF_2$ and —$OCF_2CHFCF_3$.

The invention includes compounds of formula I wherein Y is CH and Z is $OCH_3$,
i.e. fluorinated methoxyacrylic acid methyl esters (group G1), the monofluorinated representatives thereof being preferred (group G11).

The invention also includes compounds of formula I wherein
Y is N and Z is $OCH_3$,
i.e. fluorinated methoxyiminoglyoxalic acid methyl esters (group G2), the monofluorinated representatives thereof being preferred (group G22).

The invention also includes those compounds of formula I wherein
Y is N and Z is $NHCH_3$,
i.e. fluorinated methoxyiminoglyoxalic acid methyl amides (group G3), the monofluorinated representatives thereof being preferred (group G33).

The classifications of groups G11, G22 and G33 also apply to the sub-groups IA, IB and IC.

One of the preferred groups of formula I is formed by those compounds wherein
U is halogen, cyano, $C_1$–$C_8$alkyl, $C_3$–$C_6$cycloalkyl, $C_3$–$C_4$alkenyl, $C_3$–$C_4$alkenyloxyiminomethyl, $C_1$–$C_4$alkoxy, $C_1$–$C_4$alkoxyiminomethyl, $C_1$–$C_2$haloalkoxy or $C_1$–$C_2$haloalkyl, and m is 0, 1 or 2 (sub-group IA).

Within the scope of that group IA preferred compounds are those compounds wherein U is chlorine, bromine, fluorine, $C_1$–$C_4$alkyl, $C_3$–$C_6$cycloalkyl, $C_1$–$C_4$alkoxy, $C_1$–$C_2$haloalkoxy or $C_1$–$C_2$haloalkyl, and m is 0, 1 or 2 (sub-group IB).

Within that group IB preferred compounds are those compounds having the following meanings:

U is chlorine, bromine, methyl, ethyl, isopropyl, cyclopropyl, methoxy, ethoxy, difluoromethoxy, trifluoromethoxy or trifluoromethyl, and m is 1 or 2 (sub-group IC).

A preferred group of compounds are those compounds of formula I (or of group G1) wherein Y is CH and Z is $OCH_3$, X is $CH_2F$ or $CHF_2$, U is methyl, and m is 0, 1, 2, 3 or 4.

The compounds of formula I

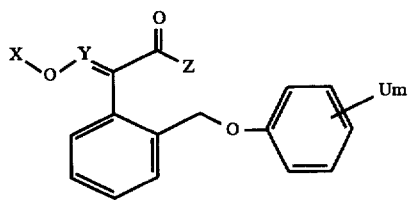

can be prepared according to the following Scheme 1, or according to Scheme 2 or according to Scheme 3.

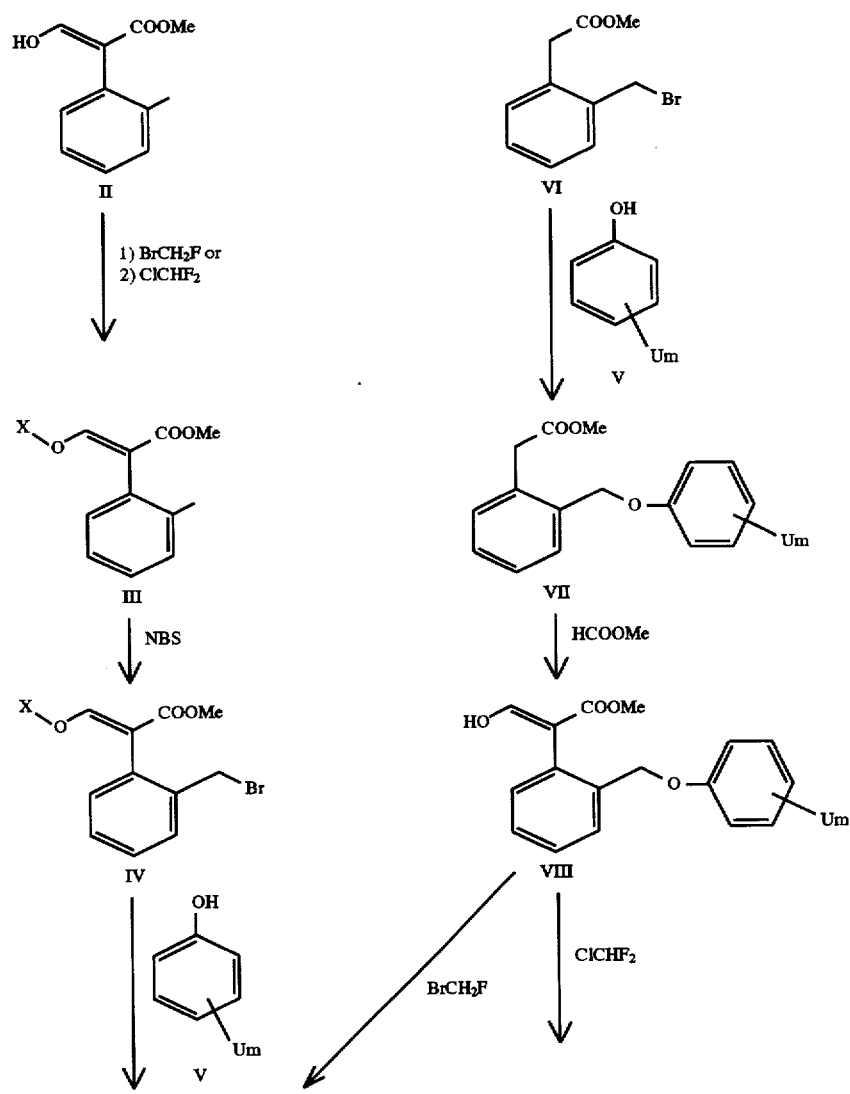

Scheme 1

-continued
Scheme 1
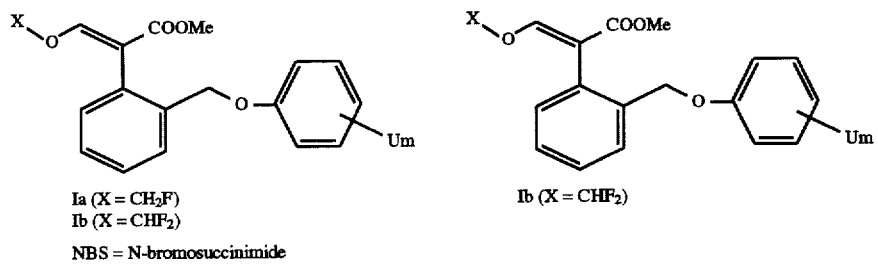
Ia (X = CH₂F)
Ib (X = CHF₂)
NBS = N-bromosuccinimide
Scheme 2
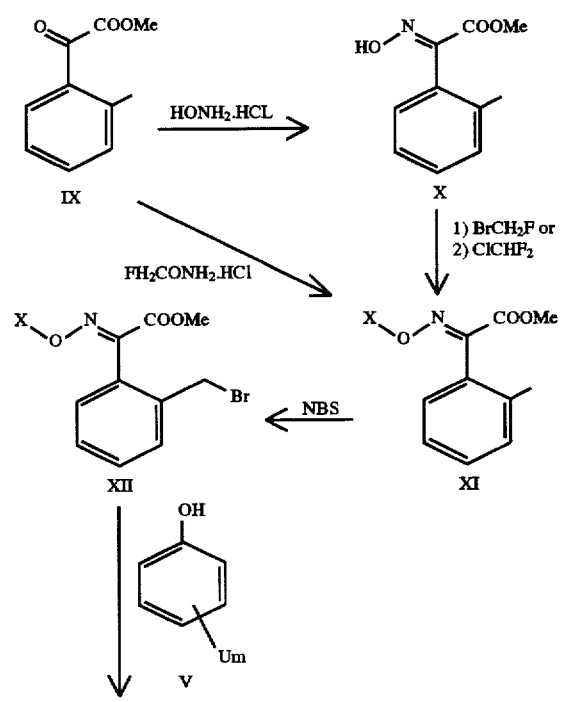
-continued
Scheme 2
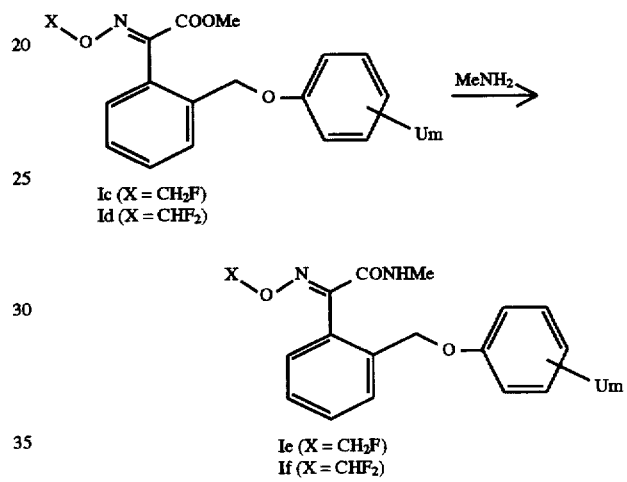
Ic (X = CH₂F)
Id (X = CHF₂)
Ie (X = CH₂F)
If (X = CHF₂)
NBS = N-bromosuccinimide
Scheme 3
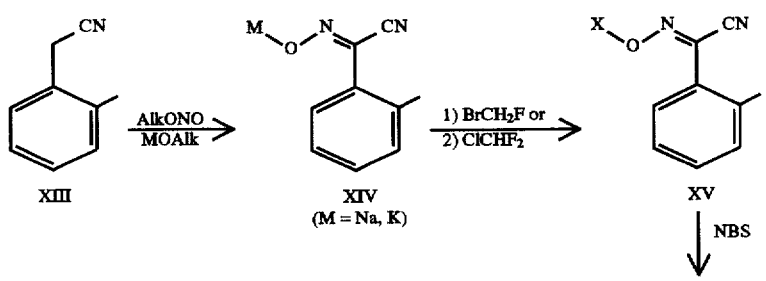

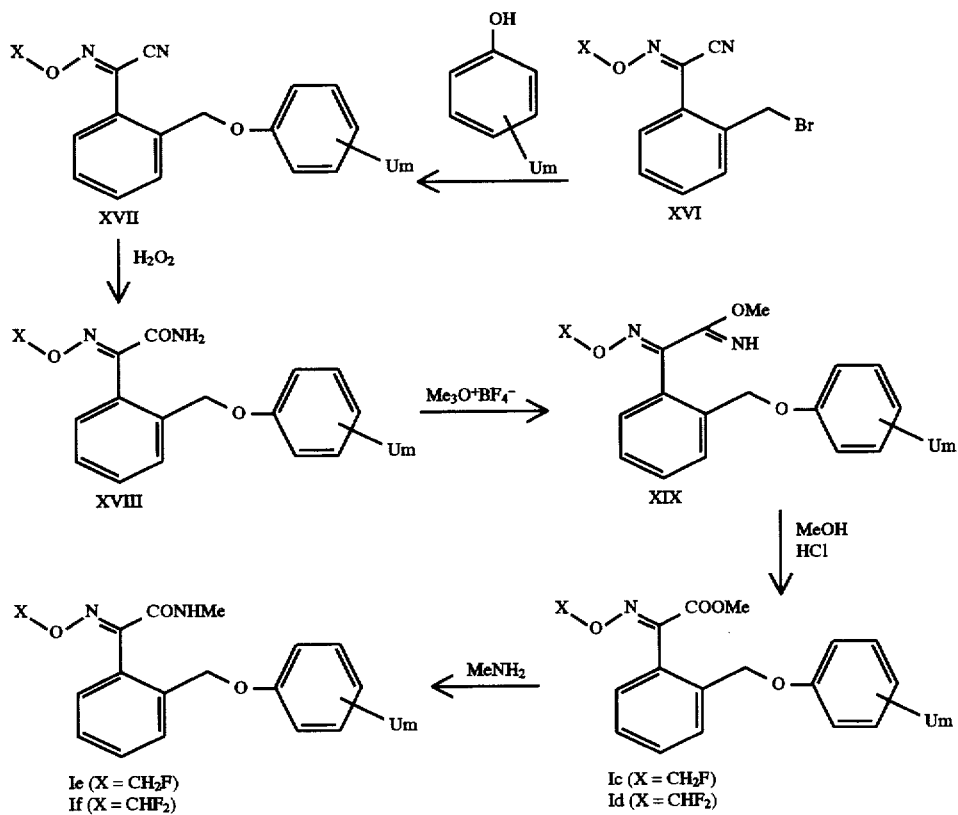

NBS = N-bromosuccinimide

The compound of formula II is known (e.g. from EP-A-178 826) and can be converted into the compound of formula III with BrCH$_2$F or with ClCHF$_2$ in an inert solvent, e.g. acetone, acetonitrile, dioxane, dimethoxyethane, dimethylformamide, dimethyl sulfoxide, tetrahydrofuran or N-methylpyrrolidone, using a suitable base, e.g. potassium hydroxide, sodium hydroxide, potassium carbonate, sodium carbonate, an alkali metal alcoholate or sodium hydride. The bromides of formula IV are obtained by bromination with N-bromosuccinimide. End products of formula Ia are obtained by reacting the bromide IV (X is CH$_2$F) with phenols of formula V.

End products of formulae Ia and Ib can also be prepared by first of all reacting a bromide of formula VI (cf. e.g. L. Chauffe et al., J. Org. Chem. 31, 3759 (1966)) with a phenol of formula V, converting the resulting benzylphenyl ether of formula VII into the enol of formula VIII in known manner by formic acid ester condensation and finally etherifying with BrCH$_2$F or ClCHF$_2$.

The compound of formula IX is known (cf. e.g. J. M. Photis, Tetrahedron Lett., 3539 (1980)) and can be converted according to known methods into the oxime of formula X which, as shown above, yields the compounds of formula XI with BrCH$_2$F or ClCHF$_2$ in inert solvents and with suitable bases.

o-Tolylglyoxalic acid methyl ester O-fluoromethyl oxime of formula XI wherein X is CH$_2$F can be prepared also directly from the o-tolylglyoxalic acid methyl ester of formula IX with O-fluoromethylhydroxylamine hydrochloride (cf. e.g. EP-A-333 154). The oxime ethers of formula XI can be brominated with N-bromosuccinimide to form compounds of formula XII and can then be converted by means of phenols of formula V into the compounds of formula Ic or Id according to the invention. Treatment of the compounds of formula Ic or Id with methylamine results in known manner in the compounds of formula Ie or If.

The compounds of formula Ic, Id, Ie or If can also be prepared by oximating 2-methylbenzyl cyanide (formula XIII) in a manner known per se (cf. e.g. Houben-Weyl, Volume 10/4, pp. 28–32) with an alkyl nitrite, e.g. ethyl, tert-butyl or isoamyl nitrite, in the presence of a suitable base, e.g. sodium ethanolate or potassium ethanolate or potassium tert-butanolate and reacting the resulting metal salt of formula XIV with BrCH$_2$F or with ClCHF$_2$ as described above to form compounds of formula XV, which are important intermediates and are novel. Bromination of the compounds of formula XV with N-bromosuccinimide results in the likewise important novel intermediates of formula XVI. When the compounds of formula XVI are reacted with phenols of formula V the compounds of formula XVII are obtained. Finally the cyano group is converted by known chemical reactions into the desired COOMe or CONHMe function to form the important compound groups of formulae Ic, Id, Ie and If.

The following compounds which are used as intermediates in the preparation of compounds of formula I are novel and form part of the present invention.

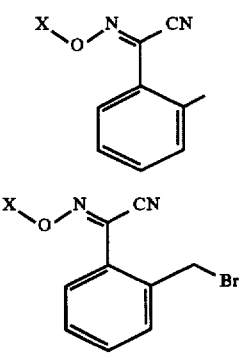

wherein X is $CH_2F$ or $CHF_2$.

It has now been found that compounds of formula I, which differ from benzylphenyl ethers from the literature inter alia by the novel structural element $FH_2C$—O— or $F_2HC$—O—, have for practical requirements an especially advantageous microbicidal spectrum in the control of phytopathogenic microorganisms, especially fungi. They have very advantageous curative, preventive and especially systemic properties and can be used in the protection of numerous cultivated plants. With the compounds of formula I it is possible to inhibit or destroy pests occurring on plants or on parts of plants (fruit, blossom, leaves, stems, tubers, roots) in various crops of useful plants, while at the same time parts of the plants which grow later are also protected from phytopathogenic microorganisms.

The compounds of formula I can also be used as dressings for protecting seed (fruits, tubers, grains) and plant cuttings against fungus infections and also against phytopathogenic fungi occurring in the soil.

Compounds of formula I are effective, for example, against the phytopathogenic fungi belonging to the following classes: *Fungi imperfecti* (especially Botrytis, and also Pyricularia, Helminthosporium, Fusarium, Septoria, Cercospora, Cercosporella and Alternaria); Basidiomycetes (e.g. Rhizoctonia, Hemileia, Puccinia). Furthermore they are effective against the class of the Ascomycetes (e.g. Venturia and Erysiphe, Podosphaera, Monilinia, Uncinula), but more especially also against the class of the Oomycetes (e.g. Phytophthora, Peronospora, Bremia, Pythium, Plasmopara).

Target crops to be protected within the scope of the present invention comprise, for example, the following species of plants: cereals (wheat, barley, rye, oats, triticale, rice, maize, sorghum and related species); beet (sugar beet and fodder beet); pomes, drupes and soft fruit (apples, pears, plums, peaches, almonds, cherries, strawberries, gooseberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor) or plants such as tobacco, nuts, coffee, sugar cane, tea, pepper and other spice plants, vines, hops, aubergines, bananas and natural rubber plants, as well as ornamentals.

Compounds of formula I are customarily used in the form of compositions and can be applied to the crop area or plant to be treated simultaneously or in succession with other active ingredients. Those other active ingredients can be either fertilizers, micronutrient donors or other compositions that influence plant growth. It is also possible to use at the same time selective herbicides and insecticides, fungicides, bactericides, nematicides, molluscicides or mixtures of several of these compositions, if desired together with other carriers, surfactants or other application-promoting adjuvants customarily employed in formulation technology.

Suitable carriers and adjuvants can be in solid or liquid form and am substances ordinarily employed in formulation technology, e.g. natural or regenerated mineral substances, solvents, dispersants, wetting agents, tackifiers, thickening agents, binders or fertilizers.

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers, such as calcite, talcum, kaolin, montmorillonite or attapulgite.

Especially advantageous application-promoting adjuvants, which can result in a significant reduction in the rate of application, are also natural (animal or vegetable) or synthetic phospholipids from the series of the cephalins and lecithins, which can be obtained, for example, from soybeans.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil; mention may also be made of fatty acid methyltaurin salts.

Suitable non-ionic surfactants are polyglycol ether derivatives of aliphatic or cycloaliphatic alcohols, saturated or unsaturated fatty acids and alkylphenols, it being possible for said derivatives to contain 3 to 30 glycol ether groups and 8 to 20 carbon atoms in the (aliphatic) hydrocarbon moiety and 6 to 18 carbon atoms in the alkyl moiety of the alkylphenols.

Representative examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable nonionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals.

The anionic, non-ionic or cationic surfactants customarily used in formulation technology are known to the person skilled in the art or can be found in the relevant specialist literature:

"Mc Cutcheon's Detergents and Emulsifiers Annual", Mc Publishing Corp., Glen Rock, N.J., 1988.

M. and J. Ash, "Encyclopedia of Surfactants", Vol. I–III, Chemical Publishing Co., New York, 1980–1981.

Dr. Helmut Stache "Tensid-Taschenbuch", Carl Hanser Verlag, Munich/Vienna 1981.

The agrochemical compositions usually comprise 0.1 to 99%, preferably 0.1 to 95%, of a compound of formula I, 99.9 to 1%, preferably 99.9 to 5%, of a solid or liquid adjuvant and 0 to 25%, preferably 0.1 to 25%, of a surfactant.

Whereas commercial products are preferably formulated as concentrates, the end user will normally employ dilute formulations.

The compositions may also comprise further ingredients, such as stabilisers, anti-foams, viscosity regulators, binders and tackifiers, as well as fertilisers or other active ingredients for obtaining special effects.

The formulations, i.e. the compositions, preparations or mixtures comprising the compound of formula I and, where appropriate, a solid or liquid adjuvant, are prepared in known manner, e.g. by homogeneously mixing and/or grinding the active ingredient with an extender, e.g. a solvent (mixture), a solid carrier and, where appropriate, surface-active compounds (surfactants).

A preferred method of applying a compound of formula I, or an agrochemical composition comprising at least one of those compounds, is application to the leaves (foliar application). The frequency and the rate of application depend on the risk of infestation by the pathogen in question. The compounds of formula I can, however, also penetrate the plants through the roots via the soil (systemic action) if the locus of the plants is impregnated with a liquid formulation or if the compounds are introduced in solid form into the soil, e.g. in the form of granules (soil application). In paddy rice crops, such granules may be applied in metered amounts to the flooded rice field. The compounds of formula I may also, however, be applied to the seeds (coating) either by impregnating the seeds with a liquid formulation of the compound or by coating them with a solid formulation. In principle, any kind of plant propagation material can be protected with the compounds of formula I, e.g. seeds, rooks or stems.

The compounds of formula I are used in unmodified form or preferably together with the adjuvants conventionally employed in formulation technology. They are for that purpose advantageously formulated in known manner e.g. into emulsifiable concentrates, coatable pastes, directly sprayable or dilutable solutions, dilute emulsions, wettable powders, soluble powders, dusts, granules, or encapsulations in e.g. polymer materials. As with the nature of the compositions, the methods of application, such as spraying, atomising, dusting, scattering, coating or pouring, are chosen in accordance with the intended objectives and the prevailing circumstances. Advantageous rates of application are generally from 5 g to 2 kg of active ingredient (a.i.) per hectare, preferably from 25 g to 800 g a.i./ha and most preferably from 50 g to 400 g a.i./ha. When used as seed dressings, rates of from 0.001 g to 1.0 g of active ingredient per kg of seed are advantageously used.

The Examples that follow further illustrate, but do not limit, the invention.

Preparation examples:

EXAMPLE P-1

Preparation of

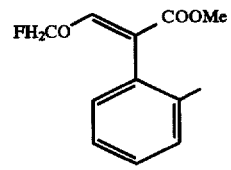

A solution of 14.9 g of bromofluoromethane in 20 ml of dimethylformamide is added dropwise at 10° C. to a solution of 20 g of the sodium salt of 3-hydroxy-2-(o-tolyl)-acrylic acid methyl ester in 125 ml of dimethylformamide and the reaction mixture is then stirred at room temperature for 2.5 hours. The reaction mixture is then poured onto 400 ml of ice-water and exhaustive extraction is carried out with ethyl acetate. Washing with saturated sodium chloride solution is followed by drying over sodium sulfate, filtering and concentration by evaporation. Chromatography on silica gel with hexane/ethyl acetate (6:1) yields pure 3-fluoromethoxy-2-(o-tolyl)-acrylic acid methyl ester in the form of a colourless oil.

$^1$H-NMR (CDCl$_3$) δ ppm: 2.19 (s, 3H), 3.73 (s, 3H), 5.45 (d, 2H, J=52 Hz), 7.11–7.27 (m, 4H), 7.70 (s, 1H)

EXAMPLE P-2

Preparation of

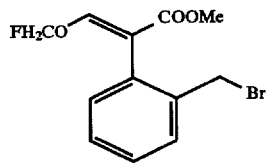

11.75 g of N-bromosuccinimide are added in several small portions, under reflux, to a solution of 14.75 g of 3-fluoromethoxy-2-(o-tolyl)-acrylic acid methyl ester and 0.53 g of dibenzoyl peroxide in 90 ml of carbon tetrachloride and then the mixture is refluxed for a further 0.5 hour. The suspension is cooled to room temperature, filtered and concentrated to dryness by evaporation. Chromatography on silica gel with hexane/ethyl acetate (6:1) yields pure 2-(2-bromomethylphenyl)-3-fluoromethoxy-acrylic acid methyl ester; m.p. 73°–76° C.

EXAMPLE P-3

Preparation of

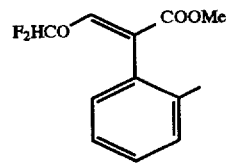

7.76 g of the sodium salt of 3-hydroxy-2-(o-tolyl)-acrylic acid methyl ester and 0.3 g of 15-crown-5 in 160 ml of N-methyl-2-pyrrolidone (NMP) are cooled to 5° C. with stirring. Chlorodifluoromethane is then passed in while simultaneously adding dropwise a solution of 8.5 g of sodium hydroxide in 9.3 ml of water and the reaction mixture is left to react with vigorous stirring at 5°–8° C. for 2 hours. 82 ml of 2N hydrochloric acid are then added dropwise at 0°–8° C. and the phases are separated. The aqueous phase is extracted exhaustively with ethyl acetate and the combined organic phases are washed with a saturated sodium chloride solution. After drying over sodium sulfate, the residue is filtered and concentrated to dryness by evaporation in vacuo. 3-difluoromethoxy-2-(o-tolyl)acrylic acid methyl ester is obtained in the form of a pale yellow oil.

$^1$H-NMR (CDCl$_3$) δ ppm: 2.18 (s, 3H), 3.75 (s, 3H), 6.36 (t, 1H, 70 Hz), 7.13–7.32 (m, 4H), 7.89 (s, 1H).

EXAMPLE P-4

Preparation of

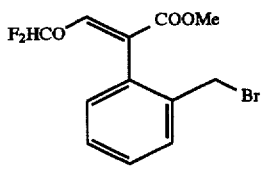

A solution of 14.2 g of 3-difluoromethoxy-2-(o-tolyl)-acrylic acid methyl ester and 0.15 g of dibenzoyl peroxide in 85 ml of carbon tetrachloride is heated to reflux. With radiation from a lamp, 10.44 g of N-bromosuccinimide are then added in several small portions and the reaction mixture is left to react for 1.5 hours. After cooling to room temperature, the reaction mixture is filtered and concentrated by evaporation in vacuo. The pale red crude product is purified by chromatography on silica gel with hexane/ethyl acetate and crystallised from hexane. Pure 2-(2-bromomethylphenyl)-3-difluoromethoxy-acrylic acid methyl ester is obtained; m.p. 63°–67° C.

EXAMPLE P-5

(Compound 1.2) Preparation of

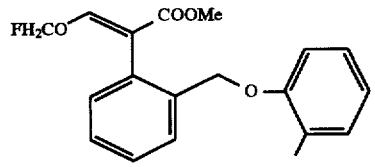

A mixture of 1.66 g of 2-(2-bromomethylphenyl)-3-fluoromethoxyacrylic acid methyl ester, 0.65 g of o-cresol, 1.38 g of pulverized potash and 0.07 g of 18-crown-6 in 15 ml of acetonitrile is stirred at room temperature for 24 hours. Water is then added, the reaction mixture is acidified with 1N hydrochloric acid and extraction is carried out with ethyl acetate. The combined organic phases are dried over sodium sulfate, filtered and concentrated by evaporation. Chromatography on silica gel with hexane/ethyl acetate yields pure 3-fluoromethoxy-2-[2-(2-methylphenoxymethyl)phenyl]-acrylic acid methyl ester in the form of a viscous oil.

$^1$H-NMR (CDCl$_3$) δ ppm: 2.27 (s, 3H), 3.73 (s, 3H), 4.97 (s, 2H), 5.45 (d, 2H), 6.75–7.64 (m, 8H), 7.72 (s, 1H) MS: m/e 330 M$^+$(8), 223 (100)

EXAMPLE P-6

Preparation of

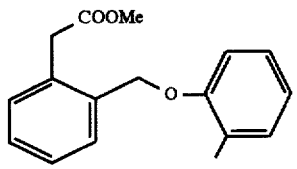

5.12 g of o-cresol and 7.2. g of pulverized potash in 30 ml of acetonitrile are preheated to 60° C. and a solution of 11.06 g of 2-(bromomethyl)-phenylacetic acid methyl ester in 35 ml of acetonitrile is added dropwise over a period of 8 minutes. The reaction mixture is then stirred for 4 minutes and immediately poured onto ice-water and weakly acidified with 2N hydrochloric acid. The aqueous solution is extracted exhaustively with ethyl acetate and the combined organic phases are washed with water, dried over sodium sulfate, filtered and concentrated by evaporation. Chromatography on silica gel with hexane/ethyl acetate (9:1) yields pure 2-(2-methylphenoxymethyl)-phenylacetic acid methyl ester in the form of a pale yellow oil.

$^1$H-NMR (CDCl$_3$) δ ppm: 2.24 (s, 3H), 3.64 (s, 3H), 3.75 (s, 2H), 5.07 (s, 2H), 6.80–7.47 (m, 8H)

EXAMPLE P-7

Preparation of

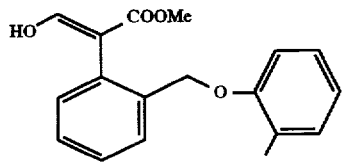

A solution of 6.9 g of 2-(2-methylphenoxymethyl)-phenylacetic acid methyl ester and 6.2 g of formic acid methyl ester in 32 ml of tert-butyl methyl ether is added dropwise at room temperature to a suspension of 1.22 g (51 mmol) of sodium hydride in 18 ml of tert-butyl methyl ether. The reaction starts immediately with slight H$_2$ evolution. The reaction mixture is then stirred at room temperature for a further 7 hours. For working up, the reaction mixture is cooled to 0°–5° C., approx. 5 ml of methanol are added and after approx. 30 minutes it is poured onto ice-water. Acidification is carried out with acetic acid and extraction is carried out exhaustively with ethyl acetate. The combined organic phases are washed with a sodium chloride solution, dried over sodium sulfate, filtered and concentrated to dryness by evaporation in vacuo; orange-brown viscous oil that can be used in the subsequent stage without further purification.

$^1$H-NMR (CDCl$_3$) δ ppm: 2.24 (d, 3H), 3.71 (d, 3H), 4.93 (d, 2H), 6.7–7.72 (m, 9H), 11.9 (d, 1H)

EXAMPLE P-8

(Compound 2.2) Preparation of

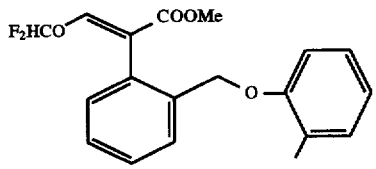

With vigorous stirring at 5° C., chlorodifluoromethane is passed into a solution of 5.7 g of 3-hydroxy-2-[2-(2-methylphenoxymethyl)phenyl]-acrylic acid methyl ester and 0.19 g of 15-crown-5 in 95 ml of N-methylpyrrolidone while simultaneously adding dropwise a solution of 5.34 g of sodium hydroxide in 6.7 ml of water and the reaction mixture is left to react for 1.5 hours. The reaction mixture is then poured onto ice-water, acidified with 4N hydrochloric acid and extracted exhaustively with ethyl acetate. The combined organic phases are washed with a sodium chloride solution, dried over sodium sulfate, filtered and concentrated by evaporation. Chromatography on silica gel with hexane/ethyl acetate (9:1) yields pure 3-difluoromethoxy-2-[2-(2-methylphenoxymethyl)phenyl]-acrylic acid methyl ester in the form of a highly viscous oil that crystallises upon being left to stand. M.p.: sinlets from 68° C., clear molten at 77° C. MS: role 348 M+ (6), 241 (100)

EXAMPLE P-9

Preparation of

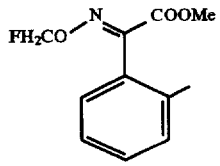

57 g of [E/Z]-o-tolylglyoxalic acid methyl ester oxime and 80 g of pulverized potash are placed in 550 ml of dimethyl sulfoxide and then stirred for 30 minutes. A solution of 40 g of bromofluoromethane in 30 ml of dimethyl sulfoxide is then added dropwise at 20° C. After 20 hours, the reaction mixture is poured onto 1200 ml of water and neutralised with 230 ml of 2N hydrochloric acid. Extraction is then carried out four times, each time with 250 ml of ethyl acetate, and the combined organic phases are washed with 200 ml of saturated sodium chloride solution, dried over sodium sulfate and concentrated by evaporation. Chromatography on silica gel with hexane/ethyl acetate (9:1) yields pure [E/Z]-o-tolylglyoxalic acid methyl ester O-fluoromethyl oxime in the form of a viscous oil.

$^1$H-NMR (CDCl$_3$) δ ppm: 2.23+2.47 (s,s, 3H, [Z+E]), 3.89+3.90 (s,s, 3H, [Z+E]), 5.74 (d, 2H, J=52 Hz, [E+Z]), 7.12–7.39 (m, 4H)

EXAMPLE P-10

Preparation of

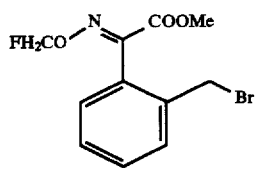

56 g of [E/Z]-o-tolylglyoxalic acid methyl ester O-fluoromethyl oxime and 0.4 g of dibenzoyl peroxide are dissolved in 350 ml of carbon tetrachloride and heated to reflux. With radiation from a lamp, 44.5 g of N-bromosuccinimide are added thereto in several small portions and the reaction mixture is then left to react for 2 hours; after cooling, the succinimide which precipitates is removed by filtration. After concentration by evaporation the residue is chromatographed on silica gel with hexane/ethyl acetate (9:1). Pure [E/Z]-2-(bromomethyl)-phenylglyoxalic acid methyl ester O-fluoromethyl oxime is obtained in the form of a viscous oil.

$^1$H-NMR (CDCl$_3$ δ ppm: 3.90 (s, 3H), 4.36+4.77 (s,s, 2H, [Z+E]), 5.75 (d, 2H), 7.16–7.53 (m, 4H)

EXAMPLE P-11

Preparation of

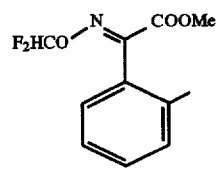

28.4 g of potassium tert-butanolate are introduced at 10°–20° C. into a solution of 19.35 g of [E/Z]-o-tolylglyoxalic acid methyl ester oxime in 250 ml of 1,2-dimethoxyethane. Once a fine suspension has been produced, chlorodifluoromethane is introduced at 25°–30° C. After 5 hours the reaction mixture is concentrated by evaporation in vacuo and water is added to the residue. The solution is weakly acidified with 2N hydrochloric acid and extraction is carried out with ethyl acetate. The combined organic phases are washed and concentrated by evaporation and the crude product is chromatographed on silica gel with hexane/ethyl acetate (5:1). Pure o-tolylglyoxalic acid methyl ester O-difluoromethyl oxime is obtained in the form of a yellow oil.

$^1$H-NMR (CDCl$_3$) δ ppm: 2.20 (s, 3H), 3.87 (s, 3H), 6.74 (t, 1H, J=70 Hz), 7.13–7.40 (m, 4H)

EXAMPLE P-12

Preparation of

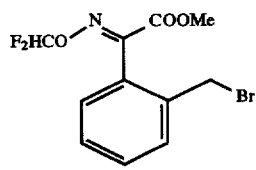

A solution of 5.1 g of o-tolylglyoxalic acid methyl ester O-difluoromethyl oxime, 0.16 g of dibenzoyl peroxide and 40 ml of carbon tetrachloride is heated to reflux. With radiation from a lamp, 3.55 g of N-bromosuccinimide are added thereto in several small portions, the mixture is left to react under reflux for 30 minutes and is then cooled to 20° C. and the succinimide which precipitates is removed by filtration. The filtrate is concentrated by evaporation; after chromatography on silica gel with hexane/ethyl acetate (6:1) pure 2-(bromomethyl)-phenylglyoxalic acid methyl ester O-difluoromethyl oxime is obtained in the form of a pale yellow oil.

$^1$H-NMR (CDCl$_3$) δ ppm: 3.93 (s, 3H), 4.35 (s, 2H), 6.77 (t, 1H, J=70 Hz), 7.19–7.58 (m, 4H).

EXAMPLE P-13

(Compound 3.2) Preparation of

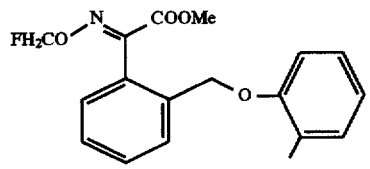

A solution of 1.84 g of o-cresol in 15 ml of dimethylformamide is added dropwise at 20° C. to a suspension of 0.4 g of sodium hydride in 5 ml of dimethylformamide. After 3 hours a solution of 5.0 g of 2-(bromomethyl)-phenylglyoxalic acid methyl ester O-fluoromethyl oxime in 25 ml of dimethylformamide is added dropwise to the brown suspension. After 16 hours 0.3 g of thiourea is added thereto and the reaction mixture is heated at 30° C. for 0.5 hour. The reaction mixture is then poured onto a saturated sodium chloride solution and extraction is carried out with ethyl acetate. The combined organic phases are washed with water, dried over sodium sulfate, filtered and concentrated by evaporation. Chromatography on silica gel with hexane/ ethyl acetate (9:1) yields pure 2-(2-methylphenoxymethyl) -phenylglyoxalic acid methyl ester O-fluoromethyl oxime; m.p. 101°–102° C.

$^1$H-NMR (CDCl$_3$) δ ppm: 2.23 (s, 3H), 3.80 (s, 3H), 4.98 (s, 2H), 5.71 (d, 2H), 6.75–7.61 (m, 8H)

EXAMPLE P-14

(Compound 3.19) Preparation of

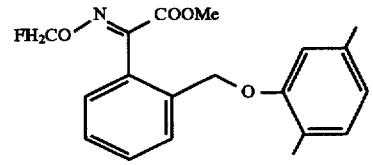

A solution of 7.0 g of 2,5-dimethylphenol in 45 ml of dimethylformamide is added dropwise at 20° C. to a suspension of 1.37 g of sodium hydride in 25 ml of dimethylfomalamide. After 3 hours a solution of 20 g of [E/Z]-2-(bromomethyl)-glyoxalic acid methyl ester O-fluoromethyl oxime in 30 ml of dimethylformamide is added dropwise to the thick, brown suspension. After subsequently stirring for 16 hours, the reaction mixture is poured onto 350 ml of saturated sodium chloride solution and extraction is carried out exhaustively with ethyl acetate. The combined organic phases are washed with water, dried over sodium sulfate, filtered and concentrated by evaporation. The two isomers of 2-(2,5-dimethylphenoxymethyl)-phenylglyoxalic acid methyl ester O-fluoromethyl oxime are separated by chromatography on silica gel with hexane/ethyl acetate (9:1). Isomer A, m.p. 45°–54° C.

$^1$H-NMR (CDCl$_3$) δ ppm: 2.27 (s, 3H), 2.30 (s, 3H), 3.92 (s, 3H), 5.28 (s, 2H), 5.72 (d, 2H), 6.66–7.82 (m, 7H)

Isomer B, m.p. 101.5°–103° C.

$^1$H-NMR (CDCl$_3$) δ ppm: 2.18 (s, 3H), 2.27 (s, 3H), 3.82 (s, 3H), 4.97 (s, 2H), 5.74 (d, 2H), 6.61–7.64 (m, 7H)

EXAMPLE P-15

(Compound 5.2) Preparation of

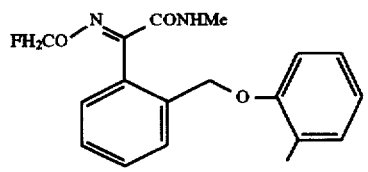

2 ml of 33% methylamine solution (in ethanol) are added to a solution of 1.02 g of 2-(2-methylphenoxymethyl)-phenylglyoxalic acid methyl ester O-fluoromethyl oxime in 30 ml of methanol and the reaction mixture is left to stand for 24 hours. Concentration by evaporation is then carried out in vacuo and the concentrate is crystallised from hexane. Pure 2-(2-methylphenoxymethyl)-phenylglyoxalic acid N-methylamide O-fluoromethyl oxime is obtained; m.p. 86°–88° C.

EXAMPLE P-16

(Compound 5.19) Preparation of

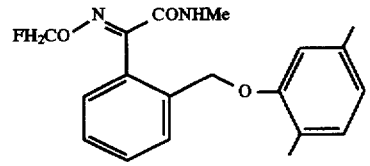

1.5 ml of 33% methylamine solution (in ethanol) are added to a solution of 1.0 g of 2-(2,5-dimethylphenoxymethyl)-phenylglyoxalic acid methyl ester O-fluoromethyl oxime in 10 ml of methanol and the reaction mixture is left to stand for 24 hours. 2-(2,5-dimethylphenoxymethyl)-phenylglyoxalic acid N-methylamide O-fluoromethyl oxime crystallises in long needles; m.p. 154°–156° C.

EXAMPLE P-17

Preparation of

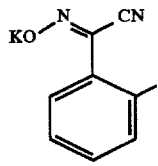

A solution of 100 g of 2-methyl-benzyl cyanide and 253 g of tert-butyl nitrite in 150 ml of tert-butanol is added dropwise at 25°–35° C. to a solution of 93 g of potassium tert-butanolate in 900 ml of tert-butanol. After 4 hours the suspension is filtered with suction and washed with tert-butyl methyl ether. After drying in vacuo, the potassium salt of α-hydroxyimino-o-tolylacetonitrile is obtained in the form of a fine, pale yellow powder; m.p. 235° C. (decomp.).

EXAMPLE P-18

Preparation of

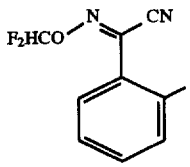

Chlorodifluoromethane is passed at 20° C. into a suspension of 18.5 g of the potassium salt of α-hydroxyimino-o-tolylacetonitrile, 1.0 g of 18-crown-6 and 185 ml of dioxane. Simultaneously a solution of 15.96 g of sodium hydroxide in 16.1 ml of water is added dropwise thereto. After subsequently stirring for 3 hours, the reaction mixture is poured onto ice-water and acidified with 2N hydrochloric acid. After extraction with ethyl acetate, the combined organic phases are washed with a saturated sodium chloride solution, dried over sodium sulfate, filtered and concentrated by evaporation. Chromatography on silica gel with hexane/ethyl acetate (9:1) yields α-difluoromethoxyimino-o-tolylacetonitrile in the form of a yellow liquid.

$^1$H-NMR (CDCl$_3$) δ ppm: 2.55 (s, 3H), 6.80 (t, 1H, J=70 Hz) 7.23–7.67 (m, 4H).

EXAMPLE P-19

Preparation of

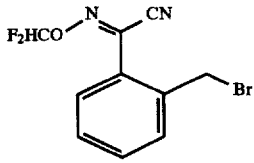

A solution of 8.0 g of α-difluoromethoxyimino-o-tolylacetonitrile and 0.07 g of dibenzoyl peroxide in 50 ml of carbon tetrachloride is heated to reflux. With radiation from a lamp, 6.77 g of N-bromosuccinimide are added thereto in several small portions and the mixture is left to react for 0.5 hour. The reaction mixture is cooled to room temperature, the succinimide is filtered off and the residue is concentrated by evaporation. Chromatography on silica gel with hexane/ethyl acetate (15:1) yields pure 2-(2-bromomethylphenyl)-2-difluoromethoxyimino-acetonitrile in the form of a pale yellow oil.

$^1$H-NMR (CDCl$_3$) δ ppm: 4.76 (s, 2H), 6.89 (t, 1H), 7.41–7.81 (m, 4H)

EXAMPLE P-20

Preparation of

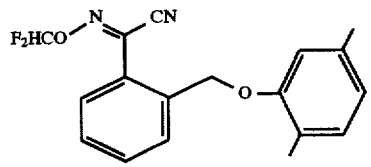

A mixture of 7.0 g of 2-(2-bromomethylphenyl)-2-difluoromethoxyimino-acetonitrile, 5.4 g of 2,5-dimethylphenol, 16.1 g of pulverized potash and 0.38 g of 18-crown-6 in 35 ml of acetonitrile is stirred at room temperature for 24 hours. For working up, water is added and exhaustive extraction with ethyl acetate is carried out. The combined organic phases are washed with saturated sodium chloride solution, dried over sodium sulfate, filtered and concentrated by evaporation. Chromatography on silica gel with hexane/ethyl acetate (9:1) yields 2-[2-(2,5-dimethylphenoxymethyl)phenyl]-2-difluoromethoxyiminoacetonitrile in the form of a sticky crystalline mass which, when treated with hexane, yields a fine crystal powder of m.p. 104°–108° C.

EXAMPLE P-21

Preparation of

A solution of 4.72 g of 2-[2-(2,5-dimethylphenoxymethyl)phenyl]-2-difluoromethoxyimino-acetonitrile in 15 ml of acetone is added dropwise to a solution of 4.88 g of hydrogen peroxide-urea adduct and 0.20 g of potassium carbonate in 15 ml of water and the reaction mixture is stirred at room temperature for 16 hours. The reaction mixture is then diluted with water and the precipitated crystalline material is filtered off with suction. Chromatography on silica gel with hexane/ethyl acetate (3:1) yields pure 2-(2,5-dimethylphenoxymethyl)-phenylglyoxalic acid amide O-difluoromethyl oxime in the form of white crystals; m.p. 153°–156° C.

MS: m/e 348 M$^+$(10), 281 (1), 227 (100)

EXAMPLE P-22

Preparation of

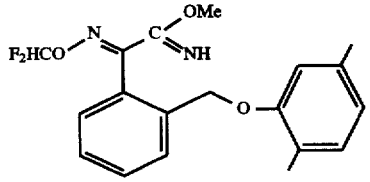

2.38 g of trimethyloxonium tetrafluoroborate are added to a suspension of 2.60 g of 2-(2,5-dimethylphenoxymethyl)-phenylglyoxalic acid amide O-difluoromethyl oxime in 70 ml of methylene chloride and the reaction mixture is stirred at room temperature for 48 hours. Ice-cold sodium carbonate solution is then added thereto, the methylene chloride phase is removed and secondary extraction is carried out with methylene chloride. The combined methylene chloride phases are washed with saturated sodium chloride solution, dried over sodium sulfate, filtered and concentrated by evaporation. 2-(2,5-dimethylphenoxymethyl)-phenylglyoxalic acid methyl ester imide O-difluoromethyl oxime crystallises from the resulting oil in the form of fine crystals; m.p. 90°–93° C.

MS: m/e 362 M⁺(5), 330 (4), 295 (36), 241 (100)

EXAMPLE P-23

(Compound 4.19) Preparation of

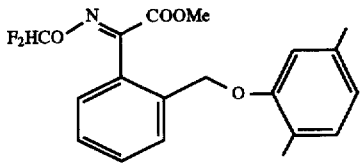

1.6 ml of 1N hydrochloric acid are added to a suspension of 1.57 g of 2-(2,5-dimethylphenoxymethyl)-phenylglyoxalic acid methyl ester imide O-difluoromethyl oxime in 20 ml of methanol. The reaction mixture is stirred with heating at 40° C. for 8 hours. For working up, water is added and exhaustive extraction with ethyl acetate is carried out. After washing the combined organic phases with sodium bicarbonate solution and water, the residue is dried over sodium sulfate, filtered and concentrated by evaporation. Chromatography on silica gel with hexane/ethyl acetate (9:1) yields 2-(2,5-dimethylphenoxymethyl)-phenylglyoxalic acid methyl ester O-difluoromethyl oxime in crystalline form; m.p. 61°–65° C.

MS: m/e 363 M⁺ (20), 331 (1), 296 (1.5), 256 (5), 242 (100).

EXAMPLE P-24

(Compound 6.19) Preparation of

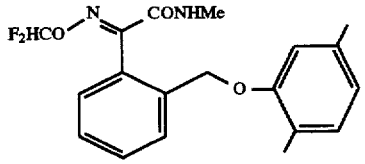

1.5 ml of 33% methylamine solution (in ethanol) are added to a solution of 0.50 g of 2-(2,5-dimethylphenoxymethyl)-phenylglyoxalic acid methyl ester O-difluoromethyl oxime in 10 ml of methanol. After being left to stand for 24 hours, 2-(2,5-dimethylphenoxymethyl)-phenylglyoxalic acid N-methylamide O-difluoromethyl oxime crystallises out. M.p. 170°–172° C.

MS: m/e 362 M⁺ (5), 295 (5), 241 (100).

In this way or in a manner analogous to one of the methods given hereinbefore, the following compounds can be prepared:

(Abbreviations: Me=Methyl, b.p.=boiling point, m.p.=melting point)

TABLE 1

| Example No. | R | Phys. data: m.p. or MS: mol peak (%)/ base peak |
|---|---|---|
| 1.1 | phenyl | 316(6), 223 |
| 1.2 | 2-Me—phenyl | 330(8), 223 |
| 1.3 | 3-Me—phenyl | |
| 1.4 | 4-Me—phenyl | |
| 1.5 | 2-Cl—phenyl | |
| 1.6 | 3-Cl—phenyl | |
| 1.7 | 4-Cl—phenyl | |
| 1.8 | 2-Br—phenyl | |
| 1.9 | 3-Br—phenyl | |
| 1.10 | 4-Br—phenyl | |
| 1.11 | 2-F—phenyl | |
| 1.12 | 3-F—phenyl | |
| 1.13 | 4-F—phenyl | |
| 1.14 | 2-OMe—phenyl | |
| 1.15 | 3-OMe—phenyl | |
| 1.16 | 4-OMe—phenyl | |
| 1.17 | 2,3-Me₂—phenyl | 344(6.9), 223 |
| 1.18 | 2,4-Me₂—phenyl | 93–94° C. |
| 1.19 | 2,5-Me₂—phenyl | 65–68° C. |
| 1.20 | 2,6-Me₂—phenyl | 98–99° C. |
| 1.21 | 2,3-Cl₂—phenyl | |
| 1.22 | 2,4-Cl₂—phenyl | |
| 1.23 | 2,5-Cl₂—phenyl | |
| 1.24 | 2,6-Cl₂—phenyl | |
| 1.25 | 3,4-Cl₂—phenyl | |
| 1.26 | 3,5-Cl₂—phenyl | |
| 1.27 | 2-Cl—, 4-Me—phenyl | |
| 1.28 | 2-Cl—, 5-Me—phenyl | |
| 1.29 | 2-Me—, 4-Cl—phenyl | |
| 1.30 | 2-Me—, 5-Cl—phenyl | |
| 1.31 | 2-F—, 4-Me—phenyl | |
| 1.32 | 2-F—, 5-Me—phenyl | |
| 1.33 | 2-Me—, 4-F—phenyl | |
| 1.34 | 2-Me—, 5-F—phenyl | |
| 1.35 | 2-Me—, 4-methoxyimino—phenyl | |
| 1.36 | 2-Me—, 5-methoxyimino—phenyl | |
| 1.37 | 2-Me—, 4-ethoxyimino—phenyl | |
| 1.38 | 2-Me—, 5-ethoxyimino—phenyl | |
| 1.39 | 2,5-Me₂—, 4-ethoxyimino—phenyl | |
| 1.40 | 2-Me—, 4-n-butoxyimino—phenyl | |
| 1.41 | 2,5-Me₂—, 4-butoxyimino—phenyl | |
| 1.42 | 2-Me—, 4-allyloxyimino—phenyl | |
| 1.43 | 2,5-Me₂—, 4-allyloxyimino—phenyl | |
| 1.44 | 2-CF₃—phenyl | |
| 1.45 | 3-CF₃—phenyl | |
| 1.46 | 4-CF₃—phenyl | |
| 1.47 | 3,5-bis(CF₃)—phenyl | |
| 1.48 | 2-Cl, 5-CF₃—phenyl | |
| 1.49 | 1-naphthyl | |
| 1.50 | 4-Cl—naphthyl | |
| 1.51 | 1-decalinyl | |
| 1.52 | 4-Cl—benzyl | |
| 1.53 | 3,4-Me₂—phenyl | 98–99° C. |
| 1.54 | 3,5-Me₂—phenyl | 344(13), 223 |
| 1.55 | 3-Cl, 2-Me—phenyl | 92–93° C. |
| 1.56 | 4-Cl, 2-Me—phenyl | 105–106° C. |

TABLE 2

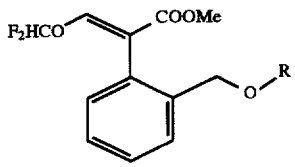

| Example No. | R | Phys. data: m.p. or MS: mol peak (%)/ base peak |
|---|---|---|
| 2.1 | phenyl | 334(4), 241 |
| 2.2 | 2-Me—phenyl | 348(6), 241 |
| 2.3 | 3-Me—phenyl | |
| 2.4 | 4-Me—phenyl | |
| 2.5 | 2-Cl—phenyl | |
| 2.6 | 3-Cl—phenyl | |
| 2.7 | 4-Cl—phenyl | |
| 2.8 | 2-Br—phenyl | |
| 2.9 | 3-Br—phenyl | |
| 2.10 | 4-Br—phenyl | |
| 2.11 | 2-F—phenyl | |
| 2.12 | 3-F—phenyl | |
| 2.13 | 4-F—phenyl | |
| 2.14 | 2-OMe—phenyl | |
| 2.15 | 3-OMe—phenyl | |
| 2.16 | 4-OMe—phenyl | |
| 2.17 | 2,3-$Me_2$—phenyl | 67–68° C. |
| 2.18 | 2,4-$Me_2$—phenyl | 77–78° C. |
| 2.19 | 2,5-$Me_2$—phenyl | 81–85° C. |
| 2.20 | 2,6-$Me_2$—phenyl | 362(1.35), 241 |
| 2.21 | 2,3-$Cl_2$—phenyl | |
| 2.22 | 2,4-$Cl_2$—phenyl | |
| 2.23 | 2,5-$Cl_2$—phenyl | |
| 2.24 | 2,6-$Cl_2$—phenyl | |
| 2.25 | 3,4-$Cl_2$—phenyl | |
| 2.26 | 3,5-$Cl_2$—phenyl | |
| 2.27 | 2-Cl—, 4-Me—phenyl | |
| 2.28 | 2-Cl—, 5-Me—phenyl | |
| 2.29 | 2-Me—, 4-Cl—phenyl | |
| 2.30 | 2-Me—, 5-Cl—phenyl | |
| 2.31 | 2-F—, 4-Me—phenyl | |
| 2.32 | 2-F—, 5-Me—phenyl | |
| 2.33 | 2-Me—, 4-F—phenyl | |
| 2.34 | 2-Me—, 5-F—phenyl | |
| 2.35 | 2-Me—, 4-methoxyimino—phenyl | |
| 2.36 | 2-Me—, 5-methoxyimino—phenyl | |
| 2.37 | 2-Me—, 4-ethoxyimino—phenyl | |
| 2.38 | 2-Me—, 5-ethoxyimino—phenyl | |
| 2.39 | 2,5-$Me_2$—, 4-ethoxyimino—phenyl | |
| 2.40 | 2-Me—, 4-n-butoxyimino—phenyl | |
| 2.41 | 2,5-$Me_2$—, 4-butoxyimino—phenyl | |
| 2.42 | 2-Me—, 4-allyloxyimino—phenyl | |
| 2.43 | 2,5-$Me_2$—, 4-allyloxyimino—phenyl | |
| 2.44 | 2-$CF_3$—phenyl | |
| 2.45 | 3-$CF_3$—phenyl | |
| 2.46 | 4-$CF_3$—phenyl | |
| 2.47 | 4-$CH_3$—benzyl | |
| 2.48 | 4-phenoxyphenyl | |
| 2.49 | 3,4-$Me_2$—phenyl | 362(17), 241 |
| 2.50 | 3,5-$Me_2$—phenyl | |
| 2.51 | 3-Cl, 2-Me—phenyl | |
| 2.52 | 4-Cl, 2-Me—phenyl | |

TABLE 3

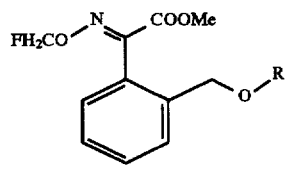

| Example No. | R | Phys. data: m.p. or MS: mol peak (%)/ base peak |
|---|---|---|
| 3.1 | phenyl | |
| 3.2 | 2-Me—phenyl | 101–102° C. |
| 3.3 | 3-Me—phenyl | |
| 3.4 | 4-Me—phenyl | |
| 3.5 | 2-Cl—phenyl | |
| 3.6 | 3-Cl—phenyl | |
| 3.7 | 4-Cl—phenyl | |
| 3.8 | 2-Br—phenyl | |
| 3.9 | 3-Br—phenyl | |
| 3.10 | 4-Br—phenyl | |
| 3.11 | 2-F—phenyl | |
| 3.12 | 3-F—phenyl | |
| 3.13 | 4-F—phenyl | |
| 3.14 | 2-OMe—phenyl | |
| 3.15 | 3-OMe—phenyl | |
| 3.16 | 4-OMe—phenyl | |
| 3.17 | 2,3-$Me_2$—phenyl | |
| 3.18 | 2,4-$Me_2$—phenyl | |
| 3.19 | 2,5-$Me_2$—phenyl | Isomer A: 45–54° C.<br>Isomer B: 101.5–103° C. |
| 3.20 | 2,6-$Me_2$—phenyl | |
| 3.21 | 2,3-$Cl_2$—phenyl | |
| 3.22 | 2,4-$Cl_2$—phenyl | |
| 3.23 | 2,5-$Cl_2$—phenyl | |
| 3.24 | 2,6-$Cl_2$—phenyl | |
| 3.25 | 3,4-$Cl_2$—phenyl | |
| 3.26 | 3,5-$Cl_2$—phenyl | |
| 3.27 | 2-Cl—, 4-Me—phenyl | |
| 3.28 | 2-Cl—, 5-Me—phenyl | |
| 3.29 | 2-Me—, 4-Cl—phenyl | |
| 3.30 | 2-Me—, 5-Cl—phenyl | |
| 3.31 | 2-F—, 4-Me—phenyl | |
| 3.32 | 2-F—, 5-Me—phenyl | |
| 3.33 | 2-Me—, 4-F—phenyl | |
| 3.34 | 2-Me—, 5-F—phenyl | |
| 3.35 | 2-Me—, 4-methoxyimino—phenyl | |
| 3.36 | 2-Me—, 5-methoxyimino—phenyl | |
| 3.37 | 2-Me—, 4-ethoxyimino—phenyl | |
| 3.38 | 2-Me—, 5-ethoxyimino—phenyl | |
| 3.39 | 2,5-$Me_2$—, 4-ethoxyimino—phenyl | |
| 3.40 | 2-Me—, 4-n-butoxyimino—phenyl | |
| 3.41 | 2,5-$Me_2$—, 4-butoxyimino—phenyl | |
| 3.42 | 2-Me—, 4-allyloxyimino—phenyl | |
| 3.43 | 2,5-$Me_2$—, 4-allyloxyimino—phenyl | |
| 3.44 | 3-$CF_3$—phenyl | |
| 3.45 | 2-Cl—benzyl | |
| 3.46 | 2-naphthyl | |

TABLE 4

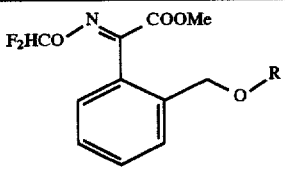

| Example No. | R | Phys. data: m.p. or MS: mol peak (%)/ base peak |
|---|---|---|
| 4.1 | phenyl | |
| 4.2 | 2-Me—phenyl | |
| 4.3 | 3-Me—phenyl | |
| 4.4 | 4-Me—phenyl | |
| 4.5 | 2-Cl—phenyl | |
| 4.6 | 3-Cl—phenyl | |
| 4.7 | 4-Cl—phenyl | |
| 4.8 | 2-Br—phenyl | |
| 4.9 | 3-Br—phenyl | |
| 4.10 | 4-Br—phenyl | |
| 4.11 | 2-F—phenyl | |
| 4.12 | 3-F—phenyl | |
| 4.13 | 4-F—phenyl | |
| 4.14 | 2-OMe—phenyl | |
| 4.15 | 3-OMe—phenyl | |
| 4.16 | 4-OMe—phenyl | |
| 4.17 | 2,3-Me$_2$—phenyl | |
| 4.18 | 2,4-Me$_2$—phenyl | |
| 4.19 | 2,5-Me$_2$—phenyl | 61–65° C. |
| 4.20 | 2,6-Me$_2$—phenyl | |
| 4.21 | 2,3-Cl$_2$—phenyl | |
| 4.22 | 2,4-Cl$_2$—phenyl | |
| 4.23 | 2,5-Cl$_2$—phenyl | |
| 4.24 | 2,6-Cl$_2$—phenyl | |
| 4.25 | 3,4-Cl$_2$—phenyl | |
| 4.26 | 3,5-Cl$_2$—phenyl | |
| 4.27 | 2-Cl—, 4-Me—phenyl | |
| 4.28 | 2-Cl—, 5-Me—phenyl | |
| 4.29 | 2-Me—, 4-Cl—phenyl | |
| 4.30 | 2-Me—, 5-Cl—phenyl | |
| 4.31 | 2-F—, 4-Me—phenyl | |
| 4.32 | 2-F—, 5-Me—phenyl | |
| 4.33 | 2-Me—, 4-F—phenyl | |
| 4.34 | 2-Me—, 5-F—phenyl | |
| 4.35 | 2-Me—, 4-methoxyimino—phenyl | |
| 4.36 | 2-Me—, 5-methoxyimino—phenyl | |
| 4.37 | 2-Me—, 4-ethoxyimino—phenyl | |
| 4.38 | 2-Me—, 5-ethoxyimino—phenyl | |
| 4.39 | 2,5-Me$_2$—, 4-ethoxyimino—phenyl | |
| 4.40 | 2-Me—, 4-n-butoxyimino—phenyl | |
| 4.41 | 2,5-Me$_2$—, 4-butoxyimino—phenyl | |
| 4.42 | 2-Me—, 4-allyloxyimino—phenyl | |
| 4.43 | 2,5-Me$_2$—, 4-allyloxyimino—phenyl | |
| 4.44 | 3,5-Cl$_2$—benzyl | |
| 4.45 | 4-(4-chlorophenoxy)—phenyl | |
| 4.46 | 2-Cl, 4-CF$_3$—phenyl | |

TABLE 5

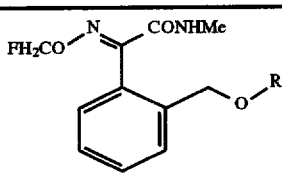

| Example No. | R | Phys. data: m.p. or MS: mol peak (%)/ base peak |
|---|---|---|
| 5.1 | phenyl | |
| 5.2 | 2-Me—phenyl | 86–88° C. |

TABLE 5-continued

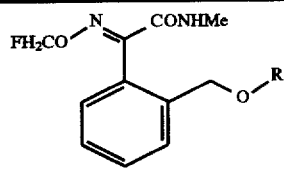

| Example No. | R | Phys. data: m.p. or MS: mol peak (%)/ base peak |
|---|---|---|
| 5.3 | 3-Me—phenyl | |
| 5.4 | 4-Me—phenyl | |
| 5.5 | 2-Cl—phenyl | |
| 5.6 | 3-Cl—phenyl | |
| 5.7 | 4-Cl—phenyl | |
| 5.8 | 2-Br—phenyl | |
| 5.9 | 3-Br—phenyl | |
| 5.10 | 4-Br—phenyl | |
| 5.11 | 2-F—phenyl | |
| 5.12 | 3-F—phenyl | |
| 5.13 | 4-F—phenyl | |
| 5.14 | 2-OMe—phenyl | |
| 5.15 | 3-OMe—phenyl | |
| 5.16 | 4-OMe—phenyl | |
| 5.17 | 2,3-Me$_2$—phenyl | |
| 5.18 | 2,4-Me$_2$—phenyl | |
| 5.19 | 2,5-Me$_2$—phenyl | 154–156° C. |
| 5.20 | 2,6-Me$_2$—phenyl | |
| 5.21 | 2,3-Cl$_2$—phenyl | |
| 5.22 | 2,4-Cl$_2$—phenyl | |
| 5.23 | 2,5-Cl$_2$—phenyl | |
| 5.24 | 2,6-Cl$_2$—phenyl | |
| 5.25 | 3,4-Cl$_2$—phenyl | |
| 5.26 | 3,5-Cl$_2$—phenyl | |
| 5.27 | 2-Cl—, 4-Me—phenyl | |
| 5.28 | 2-Cl—, 5-Me—phenyl | |
| 5.29 | 2-Me—, 4-Cl—phenyl | |
| 5.30 | 2-Me—, 5-Cl—phenyl | |
| 5.31 | 2-F—, 4-Me—phenyl | |
| 5.32 | 2-F—, 5-Me—phenyl | |
| 5.33 | 2-Me—, 4-F—phenyl | |
| 5.34 | 2-Me—, 5-F—phenyl | |
| 5.35 | 2-Me—, 4-methoxyimino—phenyl | |
| 5.36 | 2-Me—, 5-methoxyimino—phenyl | |
| 5.37 | 2-Me—, 4-ethoxyimino—phenyl | |
| 5.38 | 2-Me—, 5-ethoxyimino—phenyl | |
| 5.39 | 2,5-Me$_2$—, 4-ethoxyimino—phenyl | |
| 5.40 | 2-Me—, 4-n-butoxyimino—phenyl | |
| 5.41 | 2,5-Me$_2$—, 4-butoxyimino—phenyl | |
| 5.42 | 2-Me—, 4-allyloxyimino—phenyl | |
| 5.43 | 2,5-Me$_2$—, 4-allyloxyimino—phenyl | |
| 5.44 | 3-CF$_3$—phenyl | |
| 5.45 | 3-CF$_3$—benzyl | |
| 5.46 | 2-Cl, 5-CF$_3$—phenyl | |

TABLE 6

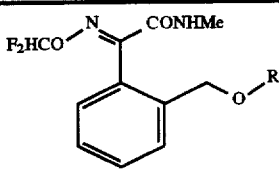

| Example No. | R | Phys. data: m.p. or MS: mol peak (%)/ base peak |
|---|---|---|
| 6.1 | phenyl | |
| 6.2 | 2-Me—phenyl | |
| 6.3 | 3-Me—phenyl | |
| 6.4 | 4-Me—phenyl | |

TABLE 6-continued

Structure: F$_2$HCO-N=C(CONHMe)-C$_6$H$_4$-CH$_2$-O-R (ortho substituted)

| Example No. | R | Phys. data: m.p. or MS: mol peak (%)/ base peak |
|---|---|---|
| 6.5 | 2-Cl—phenyl | |
| 6.6 | 3-Cl—phenyl | |
| 6.7 | 4-Cl—phenyl | |
| 6.8 | 2-Br—phenyl | |
| 6.9 | 3-Br—phenyl | |
| 6.10 | 4-Br—phenyl | |
| 6.11 | 2-F—phenyl | |
| 6.12 | 3-F—phenyl | |
| 6.13 | 4-F—phenyl | |
| 6.14 | 2-OMe—phenyl | |
| 6.15 | 3-OMe—phenyl | |
| 6.16 | 4-OMe—phenyl | |
| 6.17 | 2,3-Me$_2$—phenyl | |
| 6.18 | 2,4-Me$_2$—phenyl | |
| 6.19 | 2,5-Me$_2$—phenyl | 170–172° C. |
| 6.20 | 2,6-Me$_2$—phenyl | |
| 6.21 | 2,3-Cl$_2$—phenyl | |
| 6.22 | 2,4-Cl$_2$—phenyl | |
| 6.23 | 2,5-Cl$_2$—phenyl | |
| 6.24 | 2,6-Cl$_2$—phenyl | |
| 6.25 | 3,4-Cl$_2$—phenyl | |
| 6.26 | 3,5-Cl$_2$—phenyl | |
| 6.27 | 2-Cl—, 4-Me—phenyl | |
| 6.28 | 2-Cl—, 5-Me—phenyl | |
| 6.29 | 2-Me—, 4-Cl—phenyl | |
| 6.30 | 2-Me—, 5-Cl—phenyl | |
| 6.31 | 2-F—, 4-Me—phenyl | |
| 6.32 | 2-F—, 5-Me—phenyl | |
| 6.33 | 2-Me—, 4-F—phenyl | |
| 6.34 | 2-Me—, 5-F—phenyl | |
| 6.35 | 2-Me—, 4-methoxyimino—phenyl | |
| 6.36 | 2-Me—, 5-methoxyimino—phenyl | |
| 6.37 | 2-Me—, 4-ethoxyimino—phenyl | |
| 6.38 | 2-Me—, 5-ethoxyimino—phenyl | |
| 6.39 | 2,5-Me$_2$—, 4-ethoxyimino—phenyl | |
| 6.40 | 2-Me—, 4-n-butoxyimino—phenyl | |
| 6.41 | 2,5-Me$_2$—, 4-butoxyimino—phenyl | |
| 6.42 | 2-Me—, 4-allyloxyimino—phenyl | |
| 6.43 | 2,5-Me$_2$—, 4-allyloxyimino—phenyl | |
| 6.44 | 2-CF$_3$—phenyl | |
| 6.45 | 3-CF$_3$—phenyl | |
| 6.46 | 4-CF$_3$—phenyl | |
| 6.47 | 4-phenoxyphenyl | |

2. Formulation Examples for compounds of formula I (throughout, percentages are by weight)

| 2.1. Wettable powders | a) | b) | c) |
|---|---|---|---|
| a compound of Tables 1–6 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of any desired concentration.

| 2.2. Emulsifiable concentrate | |
|---|---|
| a compound of Tables 1–6 | 10% |
| octylphenol polyethylene glycol ether (4–5 mol of ethylene oxide) | 3% |
| calcium dodecylbenzenesulfonate | 3% |
| cyclohexanone | 34% |
| xylene mixture | 50% |

Emulsions of any required dilution can be obtained from this concentrate by dilution with water.

| 2.3. Dusts | a) | b) |
|---|---|---|
| a compound of Tables 1–6 | 5% | 8% |
| talcum | 95% | — |
| kaolin | — | 92% |

Ready-for-use dusts are obtained by mixing the active ingredient with the carrier and grinding the mixture in a suitable mill.

| 2.4. Extruder granules | |
|---|---|
| a compound of Tables 1–6 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 2.5. Coated granules | |
|---|---|
| a compound of Tables 1–6 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 2.6. Suspension concentrate | |
|---|---|
| a compound of Tables 1–6 | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired dilution can be obtained by dilution with water.

3. Biological Examples

In the following Examples B-1 to B-15 compounds according to the invention exhibit a vigorous action against fungus infestation.

EXAMPLE B-1

Action against *Phytophthora infestans* on tomato plants a) Curative action

After a cultivation period of 3 weeks, tomato plants of the variety "Red Gnome" are sprayed with a zoospore suspension of the fungus and incubated in a humidity chamber at 18° to 20° and saturated humidity. Humidifying is interrupted after 24 hours. When the plants have dried off, they are sprayed with a mixture prepared from a wettable powder formulation of the test compound at a concentration of 200 ppm. After the spray coating has dried, the plants are again placed in the humidity chamber for 4 days. The number and size of the typical leaf specks that have appeared after that time serve as a measure for evaluating the effectiveness of the tested compounds.

b) Preventive-systemic action

A wettable powder formulation of the test compound is poured at a concentration of 60 ppm (based on the volume of the soil) onto the surface of the soil in which three-week-old tomato plants of the variety "Red Gnome" have been potted. After a waiting period of three days, the undersides of the leaves of the plants are sprayed with a zoospore suspension of *Phytophthora infestans*. The treated plants are then placed in a spray cabin for 5 days at 18° to 20° C. and saturated humidity. After that period, typical leaf specks appear, the number and size of which are used to evaluate the effectiveness of the test compounds.

Whereas infestation in untreated and infected control plants is 100%, with the compounds of formula I according to one of Tables 1 to 6, for example compounds 1.1, 1.2, 1.18, 1.47, 1.48 and 2.19, infestation is reduced to 20% or less in both tests.

EXAMPLE B-2

Action against *Plasmopara viticola* (Bert. et Curt.) (Berl. et DeToni) on vines a) Residual-preventive action Vine cuttings of the variety "Chasselas" are cultivated in a greenhouse. At the 10-leaf stage, 3 plants are sprayed with a mixture comprising the active ingredient in a concentration of 200 ppm. After the spray coating has dried, the plants are uniformly infected on the undersides of the leaves with a spore suspension of the fungus. The plants are then kept in a humidity chamber for 8 days. After that time, distinct disease symptoms appear in the control plants. The number and size of the infection sites on the treated plants serve as a measure for evaluating the effectiveness of the test compounds.

b) Curative action

Vine cuttings of the variety "Chasselas" are cultivated in a greenhouse and are infected at the 10-leaf stage, on the undersides of the leaves, with a spore suspension of *Plasmopara viticola*. After being kept in a humidity chamber for 24 hours, the plants are sprayed with a mixture comprising the active ingredient in a concentration of 200 ppm. The plants are then kept in the humidity chamber for a further 7 days. After that time, the disease symptoms appear on the control plants. The number and size of the infection sites on the treated plants serve as a measure for evaluating the effectiveness of the test compounds.

In comparison with the control plants, the plants treated with compounds of formula I, e.g. compounds 1.1, 1.2, 1.18, 1.47, 1.48, 2.19 and others, exhibit an infestorion of 20% or less.

EXAMPLE B-3

Action against *Pythium debaryanum* on sugar beet (*Beta vulgaris*)

a) Action after soil application

The fungus is cultivated on sterile oat grains and added to a soil/sand mixture. The infected soil is placed in flower pots and sown with sugar beet seeds. Immediately after sowing, a wettable powder formulation of the test compounds in the form of an aqueous suspension is poured over the soil (20 ppm active ingredient based on the volume of the soil). The pots are then placed in a greenhouse for 2–3 weeks at 20°–24° C. The soil is constantly kept uniformly moist by lightly spraying with water. In evaluating the test, the emergence of the sugar beet plants and also the proportion of healthy and diseased plants is determined.

b) Action after application by dressing

The fungus is cultivated on sterile oat grains and added to a soil/sand mixture. The infected soil is placed in flower pots and sown with sugar beet seeds that have been dressed with the test compounds formulated as a dressing powder (1000 ppm active ingredient based on the weight of the seeds). The sown pots are placed in a greenhouse for 2–3 weeks at 20°–24° C., the soil being kept uniformly moist by lightly spraying with water.

In evaluating the test, the emergence of the sugar beet plants and the proportion of healthy and diseased plants is determined.

After treatment with compounds of formula I, over 80% of the plants emerge and have a healthy appearance. In the control pots, only isolated emergence of plants, which have a sickly appearance, is observed.

EXAMPLE B-4

Residual-protective action against *Cercospora arachidicola* on groundnut plants Groundnut plants 10–15 cm in height are sprayed to drip point with an aqueous spray mixture (0.02% active ingredient), and infected 48 hours later with a conidia suspension of the fungus. The infected plants are incubated for 72 hours at 21° and high humidity and then placed in a greenhouse until the typical leaf specks appear. Evaluation of the action of the active ingredient is made 12 days after infection and is based on the number and size of the leaf specks.

Compounds of formula I bring about a reduction in the leaf specks to less than about 10% of the leaf surface area. In some cases, the disease is completely suppressed (0–5% infestation).

EXAMPLE B-5

Action against *Puccinia graminis* on wheat a) Residual-protective action 6 days after sowing, wheat plants are sprayed to drip point with an aqueous spray mixture (0.02% active ingredient), and infected 24 hours later with a uredospore suspension of the fungus. After an incubation period of 48 hours (conditions: 95 to 100% relative humidity at 20°), the plants are placed in a greenhouse at 22°. Evaluation of rust pustule development is made 12 days after infection.

b) Systemic action

Wheat plants are watered 5 days after sowing with an aqueous spray mixture (0.006% active ingredient, based on the volume of the soil). Care is taken that the spray mixture does not come into contact with the parts of the plants above the soil. The treated plants are infected 48 hours later with a uredospore suspension of the fungus. After an incubation period of 48 hours (conditions: 95 to 100% relative humidity at 20°), the plants are placed in a greenhouse at 22°. Evaluation of rust pustule development is made 12 days after infection.

Compounds of formula I, for example compounds 1.1, 1.2, 1.18, 1.47, 1.48 and 2.19, bring about a distinct reduction in the fungus infestation, in some cases to 10–0%.

EXAMPLE B-6

Action against *Pyricularia oryzae* on rice plants
a) Residual-protective action After a cultivation period of 2 weeks, rice plants are sprayed to drip point with an aqueous spray mixture (0.02% active ingredient), and infected 48 hours later with a conidia suspension of the fungus. Evaluation of fungus infestation is made 5 days after infection, during which time 95 to 100% relative humidity and a temperature of 22° are maintained.
b) Systemic action 2-week-old rice plants are watered with an aqueous spray mixture (0.006% active ingredient, based on the volume of the soil). Care is taken that the spray mixture does not come into contact with the parts of the plants above the soil. The pots are then filled with water so that the lowermost parts of the stalks of the rice plants stand in water. After 96 hours, the plants are infected with a conidia suspension of the fungus and are kept for 5 days at 95 to 100% relative humidity and a temperature of 24° C.

Compounds of formula I largely prevent the outbreak of the disease on the infected plants.

EXAMPLE B-7

Residual-protective action against *Venturia inaequalis* on apples

Apple cuttings with 10–20 cm long fresh shoots are sprayed to drip point with a spray mixture (0.02% active ingredient), and infected 24 hours later with a conidia suspension of the fungus. The plants are then incubated for 5 days at 90–100% relative humidity and placed in a greenhouse for a further 10 days at 20°–24° C. Scab infestation is evaluated 15 days after infection.

Compounds of formula I of one of Tables 1 to 6 have predominantly a lasting action against scab diseases (less than 10% infestation).

EXAMPLE B-8

Action against *Erysiphe graminis* on barley
a) Residual-protective action

Barley plants about 8 cm in height are sprayed to drip point with an aqueous spray mixture (0.02% active ingredient) and dusted 3 to 4 hours later with conidia of the fungus. The infected plants are placed in a greenhouse at 22°. The fungus infestation is evaluated 10 days after infection.
b) Systemic action Barley plants about 8 cm in height are watered with an aqueous spray mixture (0.002% active ingredient, based on the volume of the soil). Care is taken that the spray mixture does not come into contact with the parts of the plants above the soil. The treated plants are dusted 48 hours later with conidia of the fungus. The infected plants are placed in a greenhouse at 22°. The fungus infestation is evaluated 10 days after infection.

Compounds of formula I in general are able to suppress infestation with the disease to less than 20% and, in some cases, to suppress it completely, e.g. compounds 1.1, 1.2, 1.18, 1.47, 1.48, 2.19 and others.

EXAMPLE B-9

Action against *Podosphaera leucotricha* on apple shoots
Residual-protective action Apple cuttings with approximately 15 cm long fresh shooks are sprayed with a spray mixture (0.06% active ingredient). The treated plants are infected 24 hours later with a conidia suspension of the fungus and are placed in a climatic chamber at 70% relative humidity and 20° C. The fungus infestation is evaluated 12 days after infection.

After treatment with compounds of formula I, e.g. compounds 1.1, 1.2, 1.18, 1.47, 1.48 and 2.19, infestation with the disease is less than 20%. Infestation in control plants is 100%.

EXAMPLE B-10

Action against *Botrytis cinerea* on apple fruit
Residual-protective action

Artificially damaged apples are treated by applying drops of a spray mixture (0.02% active ingredient) to the damage sites. The treated fruits are then inoculated with a spore suspension of the fungus and incubated for one week at high humidity and about 20° C. The fungicidal action of the test compound is derived from the number of damage sites that have begun to rot.

Compounds of formula I of Tables 1 to 6, e.g. compounds 1.1, 1.2, 1.18, 1.48 and 2.19, are able to prevent the spread of the rot in some cases completely.

EXAMPLE B-11

Action against *Helminthosporium gramineum*

Wheat grains are contaminated with a spore suspension of the fungus and left to dry. The contaminated grains are dressed with a suspension of the test compound (600 ppm of active ingredient based on the weight of the seeds). After two days, the grains are set out on suitable agar dishes and, four days later, the development of the fungus colonies around the grains is assessed. The number and size of the fungus colonies are used to evaluate the test compound.

Compounds of formula I exhibit in some cases a very good action, i.e. complete inhibition of the fungus colonies.

EXAMPLE B-12

Action against *Colletotrichum lagenarium* on cucumbers

After a cultivation period of 2 weeks, cucumber plants are sprayed with a spray mixture (concentration 0.002%). Two days later, the plants are infected with a spore suspension ($1.5 \times 10^5$ spores/ml) of the fungus and incubated for 36 hours at 23° C. and high humidity. Incubation is then continued at normal atmospheric humidity and about 22°–23° C. The fungal infestation that has occurred is evaluated 8 days after infection. Fungal infestation in untreated and infected control plants is 100%.

Compounds of formula I cause in some cases almost complete inhibition of disease infestation.

EXAMPLE B-13

Action against *Fusarium nivale* on rye

Rye of the variety Tetrahell naturally infected with *Fusarium nivale* is dressed in a roller mixer with the fungicide to be tested, the following concentrations being used: 20 or 6 ppm a.i. (based on the weight of the seed).

The infected and treated rye is sown in the open in October in plots of 3 m length and 6 seed rows using a sowing machine. 3 replicates are made for each concentration.

Until evaluation of the infestation, the test crop is cultivated under normal field conditions (preferably in a region having unbroken snow cover during the winter months).

In order to evaluate the phytotoxicity, the emergence is assessed in the autumn and the crop density/number of plants per unit area is assessed in the spring.

In order to determine the activity of the compounds, in spring, immediately after the snow has melted, the percentage proportion of plants infested with Fusarium is calculated. The number of infested plants is, in the present case, less than 5%. The emerged plants have a healthy appearance.

EXAMPLE B-14

Action against *Septoria nodorum* on wheat

Wheat plants are sprayed at the 3-leaf stage with a spray mixture (60 ppm a.i.) prepared from a wettable powder formulation of the test compounds (2.8:1). 24 hours later, the treated plants are infected with a conidia suspension of the fungus. The plants are then incubated for 2 days at 90–100% relative humidity and placed in a greenhouse at 20°–24° C. for a further 10 days. Fungus infestation is evaluated 13 days after infection. Less than 1% of the wheat plants show infestation.

EXAMPLE B-15

Action against *Rhizoctonia solani* on rice
Protective local soil application 10-day-old rice plants are watered with a suspension (spray mixture) prepared from a formulation of the test compound, without contaminating the parts of the plants above the soil. Infection is carried out three days later by placing between the rice plants in each pot a blade of barley straw infected with *Rhizoctonia solani*. Fungus infestation is evaluated after 6 days' incubation in a climatic chamber at 29° C. day temperature and 26° C. night temperature and 95% relative humidity. Less than 5% of the rice plants show infestation. The plants have a healthy appearance.
Protective local foliar application 12-day-old rice plants are sprayed with a suspension prepared from a formulation of the test compound. Infection is carried out one day later by placing between the rice plants in each pot a blade of barley straw infected with *Rhizoctonia solani*. Evaluation is made after 6 days' incubation in a climatic chamber at 29° C. day temperature and 26° C. night temperature and 95% relative humidity. Fungus infestation on untreated and infected control plants is 100%. Compounds of formula I cause in some cases almost complete inhibition of disease infestation.

What is claimed is:

1. A compound of formula I

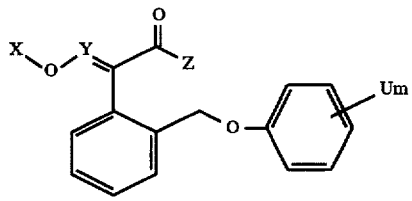

or a possible isomer or isomeric mixture thereof, wherein
a)
X is $CH_2F$ or $CHF_2$;
Y is CH and
Z is OMe, or b)
X is $CH_2F$ or $CHF_2$;
Y is a nitrogen atom and
Z is OMe or $NHCH_3$,
and wherein also
m is 0, 1, 2, 3, 4 or 5 and
U represents identical or different substituents selected from halogen, cyano, nitro, $C_1-C_{12}$alkyl, $C_3-C_8$cycloalkyl, $C_3-C_6$alkenyl, $C_3-C_6$alkenyloxyiminomethyl, $C_1-C_4$alkoxy, $C_1-C_4$alkoxyiminomethyl, $C_1-C_2$haloalkyl, $C_1-C_2$haloalkoxy, unsubstituted or substituted phenyl, unsubstituted or substituted phenoxy and unsubstituted or substituted benzyl or represents substituents at two adjacent positions of the phenyl ring of formula I that define a fused hydrocarbon bridge so as to form a larger hydrocarbon ring having up to 14 carbon atoms.

2. A compound of formula I according to claim 1 wherein
m is 0, 1 or 2, and
U is halogen, cyano, $C_1-C_8$alkyl, $C_3-C_6$cycloalkyl, $C_3-C_4$alkenyl, $C_3-C_6$alkenyloxyiminomethyl, $C_1-C_4$alkoxy, $C_1-C_4$alkoxyiminomethyl, $C_1-C_2$haloalkyl or $C_1-C_2$haloalkoxy.

3. A compound of formula I according to claim 2 wherein
U is chlorine, bromine, fluorine, $C_1-C_4$alkyl, $C_3-C_6$cycloalkyl, $C_1-C_4$alkoxy, $C_1-C_2$haloalkyl or $C_1-C_2$haloalkoxy.

4. A compound of formula I according to claim 3 wherein
m is 1 or 2, and
U is chlorine, bromine, methyl, ethyl, isopropyl, cyclopropyl, methoxy, ethoxy, difluoromethoxy, trifluoromethyl or trifluoromethoxy.

5. A compound of formula I according to claim 1 wherein
X is $CH_2F$ or $CHF_2$;
Y is CH and
Z is $OCH_3$,
and wherein also
U is methyl, and
m is 0, 1, 2, 3 or 4.

6. A process for the preparation of a compound of formula I according to claim 1, which comprises
a) when Y is CH
etherifying an enol of formula II

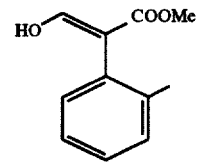

with bromofluoromethane or chlorodifluoromethane in an alkaline medium, brominating the methyl side-chain with N-bromosuccinimide to form a compound of formula IV

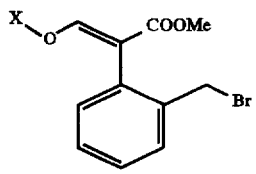

and then reacting in an alkaline medium with a phenol of formula V

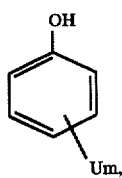

or b) when Y is CH
reacting a bromide of formula VI with a phenol of formula V and converting the ester of formula VII

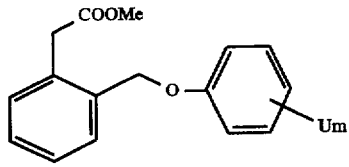

by means of formic acid ester condensation into an enol of formula VIII

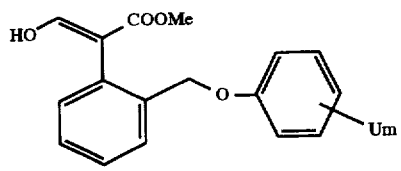

and etherifying in an alkaline medium with bromofluoromethane or chlorodifluoromethane, or c) when Y is N
etherifying an oxime of formula X

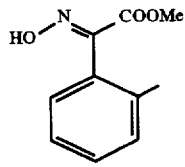

in an alkaline medium with bromofluoromethane or chlorodifluoromethane, brominating the methyl side-chain to form a compound of formula XII

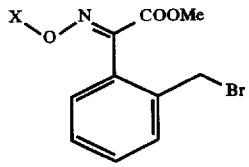

and then reacting with a phenol of formula V in an alkaline medium and, if desired, convening the methyl ester function of formulae Ic and Id by treatment with methylamine into the N-methylamide function of formulae Ie and If, respectively, or d) when Y is N
reacting an alkali metal salt of formula XIV

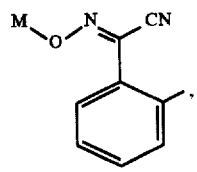

wherein M is preferably potassium or sodium, with bromofluoromethane or chlorodifluoromethane to form a compound of formula XV

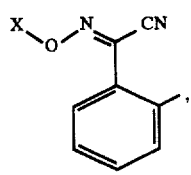

converting the methyl group by bromination into a compound of formula XVI

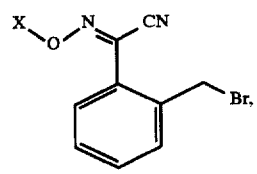

etherifying with a phenol of formula V, converting the nitrile function into the methyl ester function and, if desired, converting the latter by treatment with methylamine into the N-methylamide function.

7. A microbicidal composition comprising as active ingredient a compound of formula I according to claim 1, together with a suitable carrier.

8. A composition according to claim 7 comprising as active ingredient a compound according to any one of claims 2 to 5.

9. A process for the preparation of a composition according to claim 7 which comprises homogeneously mixing and/or grinding the active ingredient with an extender and, where appropriate, with a surface-active adjuvant.

10. A method of controlling plant diseases and of preventing infestation by micro-organisms, which comprises applying a compound of formula I according to claim 1 to the plants, to parts of the plants or to the locus of the plants.

* * * * *